(12) United States Patent
Aida et al.

(10) Patent No.: US 12,169,261 B2
(45) Date of Patent: Dec. 17, 2024

(54) RADIATION DETECTION MODULE, RADIATION DETECTOR, AND METHOD FOR MANUFACTURING RADIATION DETECTION MODULE

(71) Applicant: CANON ELECTRON TUBES & DEVICES CO., LTD., Otawara (JP)

(72) Inventors: Hiroshi Aida, Utsunomiya (JP); Hiroshi Horiuchi, Otawara (JP)

(73) Assignee: CANON ELECTRON TUBES & DEVICES CO., LTD., Otawara (JP)

( * ) Notice: Subject to any disclaimer, the term of this patent is extended or adjusted under 35 U.S.C. 154(b) by 140 days.

(21) Appl. No.: 17/667,754

(22) Filed: Feb. 9, 2022

(65) Prior Publication Data

US 2022/0163682 A1    May 26, 2022

Related U.S. Application Data

(63) Continuation of application No. PCT/JP2020/011049, filed on Mar. 13, 2020.

(30) Foreign Application Priority Data

Oct. 7, 2019  (JP) .................................. 2019-184226

(51) Int. Cl.
*G01T 1/20*     (2006.01)
(52) U.S. Cl.
CPC ........ *G01T 1/2002* (2013.01); *G01T 1/20184* (2020.05); *G01T 1/20188* (2020.05)
(58) Field of Classification Search
None
See application file for complete search history.

(56) References Cited

U.S. PATENT DOCUMENTS

| 2010/0224784 A1 | 9/2010 | Homma et al. |
| 2011/0147602 A1* | 6/2011 | Ishida ...................... G01T 1/202 |
| | | 438/57 |
| 2014/0175296 A1 | 6/2014 | Benlloch Baviera et al. |
| 2019/0113634 A1 | 4/2019 | Jonishi et al. |

(Continued)

FOREIGN PATENT DOCUMENTS

| CN | 109541669 A | 3/2019 |
| JP | 2000-9846 A | 1/2000 |
| JP | 2003-004854 A | 1/2003 |

(Continued)

OTHER PUBLICATIONS

International Search Report issued May 26, 2020 in PCT/JP2020/011049 filed on Mar. 13, 2020, 2 pages.

*Primary Examiner* — Edwin C Gunberg
(74) *Attorney, Agent, or Firm* — Oblon, McClelland, Maier & Neustadt, L.L.P.

(57) ABSTRACT

A radiation detection module according to an embodiment includes an array substrate including multiple photoelectric converters, a scintillator that covers a region in which the multiple photoelectric converters are located and that has larger dimensions than the region in which the multiple photoelectric converters are located when viewed in plan, and a light-absorbing part that is located on the scintillator and is capable of absorbing visible light. The light-absorbing part is located outward of the region in which the multiple photoelectric converters are located when viewed in plan.

11 Claims, 3 Drawing Sheets

(56) References Cited

U.S. PATENT DOCUMENTS

2020/0209412 A1\* 7/2020 Inoue .................. G01T 1/20181

FOREIGN PATENT DOCUMENTS

| JP | 2007-271504 | A  | 10/2007 |
|----|-------------|----|---------|
| JP | 2008-096344 | A  | 4/2008  |
| JP | 2009-128023 | A  | 6/2009  |
| JP | 2011-128085 | A  | 6/2011  |
| JP | 2014-106022 | A  | 6/2014  |
| JP | 2014-122898 | A  | 7/2014  |
| JP | 2019-052907 | A  | 4/2019  |
| KR | 10-2010-0085099 | A | 7/2010 |
| TW | 201307878   | A1 | 2/2013  |
| TW | 201738583   | A  | 11/2017 |

\* cited by examiner

RADIATION DETECTION MODULE, RADIATION DETECTOR, AND METHOD FOR MANUFACTURING RADIATION DETECTION MODULE

CROSS-REFERENCE TO RELATED APPLICATIONS

This application is a continuation application of International Application No. PCT/JP2020/011049, filed on Mar. 13, 2020. This application also claims the benefit of priority from Japanese Patent Application No. 2019-184226, filed on Oct. 7, 2019; the entire contents of which are incorporated herein by reference.

FIELD

Embodiments of the invention relate to a radiation detection module, a radiation detector, and a method for manufacturing a radiation detection module.

BACKGROUND

An X-ray detector is an example of a radiation detector. The X-ray detector includes a scintillator that converts X-rays into fluorescence, and an array substrate that converts the fluorescence into a charge. In such a case, multiple photoelectric converters are provided in the array substrate. The scintillator is located on a region (an effective pixel region) of the array substrate in which the multiple photoelectric converters are located.

Here, it is difficult to form only the scintillator on the effective pixel region. Therefore, the scintillator is provided also at a vicinity outside the effective pixel region. In such a case, there are cases where X-rays also are incident on the scintillator that is outside the effective pixel region. Therefore, there are cases where fluorescence is also generated by the scintillator outside the effective pixel region. Also, there are cases where light from the outside enters the scintillator.

To improve the quality of the X-ray image, it is favorable for the fluorescence that is generated above the photoelectric converters to be converted into charge. However, there are cases where the fluorescence that is generated by the scintillator outside the effective pixel region is reflected by the side surface of the scintillator, etc., and is incident on the photoelectric converters. The fluorescence that is generated by the scintillator outside the effective pixel region and the light that enters from the outside cause noise; therefore, there is a risk that the quality of the X-ray image may degrade when such light is incident on the photoelectric converters.

Therefore, it is desirable to develop technology in which the quality of the radiation image can be improved.

DETAILED DESCRIPTION

Figure 1:
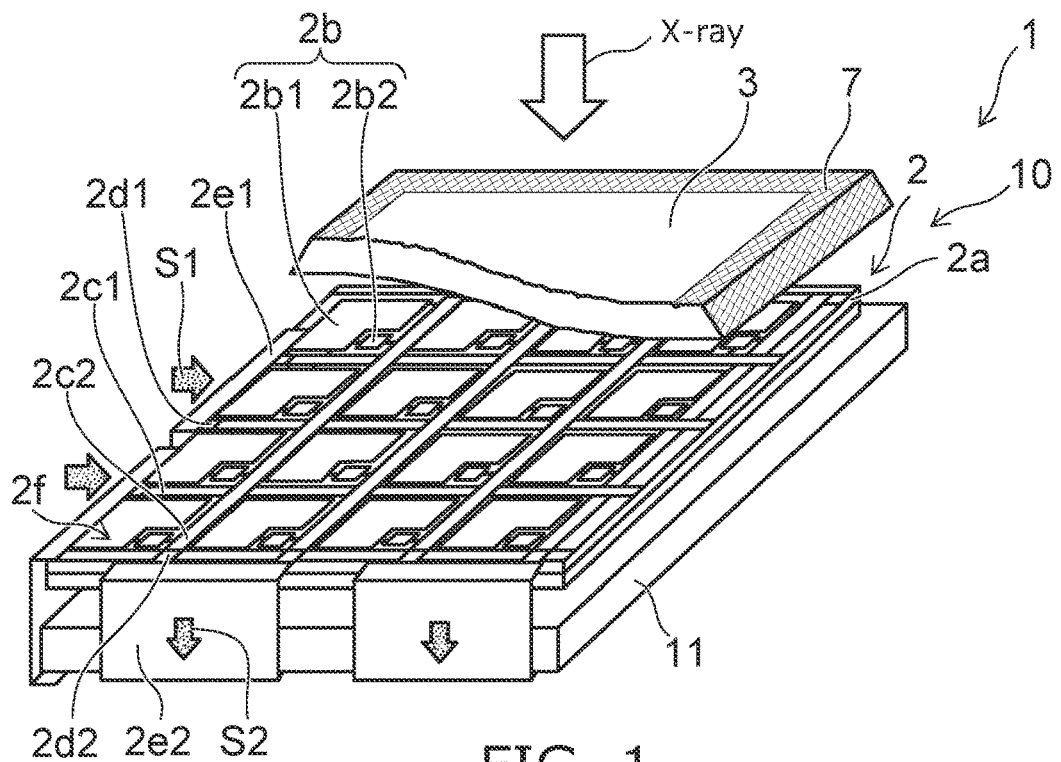
FIG. 1 is a schematic perspective view for illustrating an X-ray detector according to the embodiment.

A radiation detection module according to an embodiment includes an array substrate including multiple photoelectric converters, a scintillator that covers a region in which the multiple photoelectric converters are located and that has larger dimensions than the region in which the multiple photoelectric converters are located when viewed in plan, and a light-absorbing part that is located on the scintillator and is capable of absorbing visible light. The light-absorbing part is located outward of the region in which the multiple photoelectric converters are located when viewed in plan.

Embodiments will now be illustrated with reference to the drawings. Similar components in the drawings are marked with the same reference numerals; and a detailed description is omitted as appropriate.

Also, radiation detectors according to embodiments of the invention are applicable to various radiation other than X-rays such as γ-rays, etc. Here, as an example, the case relating to X-rays is described as a typical example of radiation. Accordingly, applications to other radiation as well are possible by replacing "X-ray" with "other radiation" in the embodiments described below.

Also, for example, the radiation detector can be used in general medical care, etc. However, the application of the radiation detector is not limited to general medical care.

Also, in the specification, "when viewed in plan" refers to when the radiation detector is viewed from the incident side of the radiation.

(X-Ray Detector 1 and X-Ray Detection Module 10)

FIG. 1 is a schematic perspective view for illustrating an X-ray detector 1 according to the embodiment.

To avoid complexity, a protective layer 2f, a reflecting part 4, a moisture-resistant part 5, a bonding part 6, etc., are not illustrated in FIG. 1.

Figure 2:
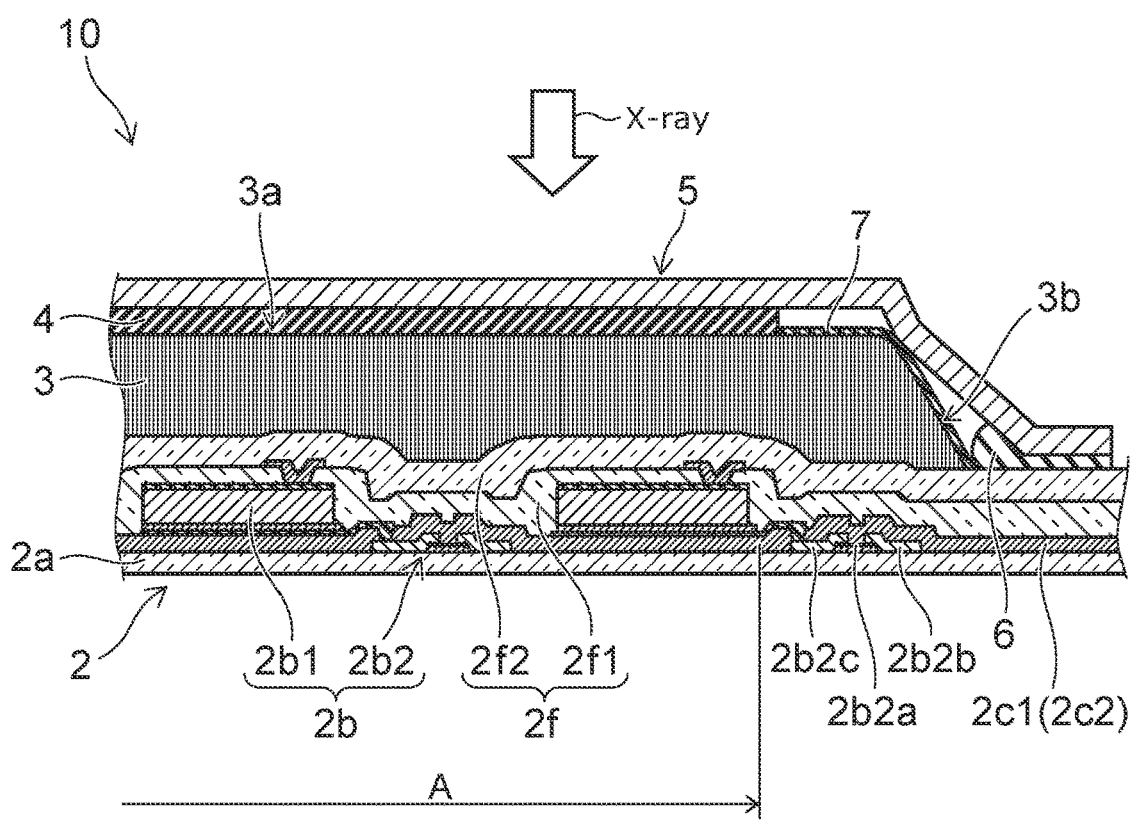
FIG. 2 is a schematic cross-sectional view for illustrating an X-ray detection module.

FIG. 2 is a schematic cross-sectional view for illustrating the X-ray detection module 10.

Figure 3:
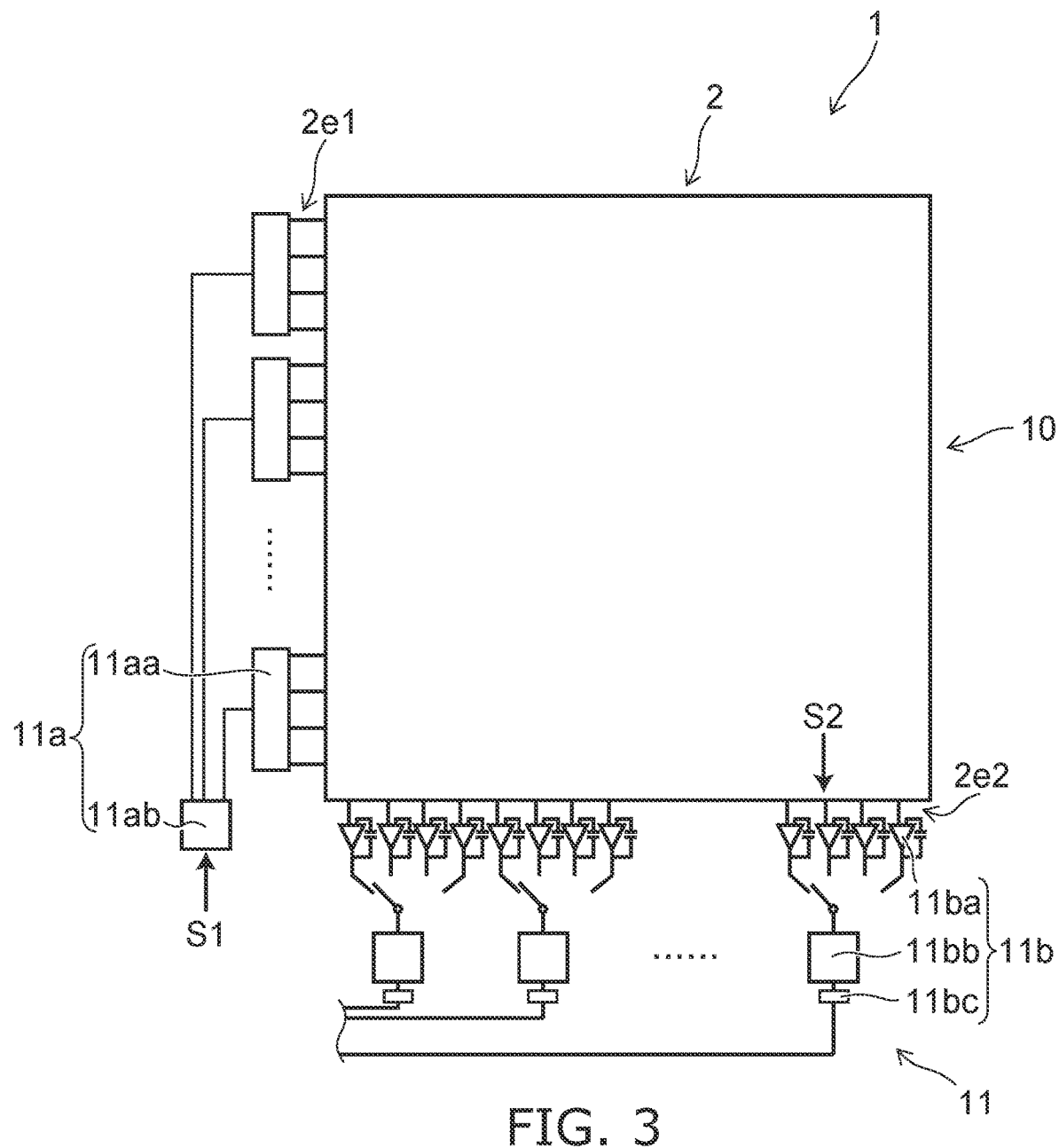
FIG. 3 is a block diagram of the X-ray detector.

FIG. 3 is a block diagram of the X-ray detector 1.

As shown in FIGS. 1 and 2, the X-ray detection module 10 and a circuit board 11 can be provided in the X-ray detector 1. Also, a not-illustrated housing can be provided in the X-ray detector 1. The X-ray detection module 10 and the circuit board 11 can be located inside the housing. For example, a plate-shaped support plate can be provided inside the housing; the X-ray detection module 10 can be located at the surface of the support plate at the incident side of the X-rays; and the circuit board 11 can be located at the surface of the support plate at the side opposite to the incident side of the X-rays.

An array substrate 2, a scintillator 3, the reflecting part 4, the moisture-resistant part 5, the bonding part 6, and a light-absorbing part 7 can be provided in the X-ray detection module 10.

A substrate 2a, a photoelectric converter 2b, a control line (or gate line) 2c1, a data line (or signal line) 2c2, an interconnect pad 2d1, an interconnect pad 2d2, and the protective layer 2f can be provided in the array substrate 2.

The numbers of the photoelectric converters 2b, the control lines 2c1, and the data lines 2c2 are not limited to those illustrated.

The substrate 2a is plate-shaped and can be formed from glass such as alkali-free glass, etc. The planar shape of the substrate 2a can be quadrilateral. The thickness of the substrate 2a can be, for example, about 0.7 mm.

Multiple photoelectric converters 2b can be located at one surface side of the substrate 2a. The photoelectric converter 2b is rectangular and can be located in a region defined by the control lines 2c1 and the data lines 2c2. The multiple photoelectric converters 2b can be arranged in a matrix configuration. For example, one photoelectric converter 2b corresponds to one pixel (pixel) of the X-ray image.

A photoelectric conversion element 2b1 and a thin film transistor (TFT; Thin Film Transistor) 2b2 that is a switching element can be provided in each of the multiple photoelectric converters 2b. Also, a not-illustrated storage capacitor that stores a signal charge converted by the photoelectric conversion element 2b1 can be provided. For example, the storage capacitor has a rectangular flat plate shape and can be located under each thin film transistor 2b2. However, the photoelectric conversion element 2b1 also can be used as the storage capacitor according to the capacitance of the photoelectric conversion element 2b1.

The photoelectric conversion element 2b1 can be, for example, a photodiode, etc.

The thin film transistor 2b2 can switch between storing and discharging the charge to and from the storage capacitor. The thin film transistor 2b2 can include a gate electrode 2b2a, a drain electrode 2b2b, and a source electrode 2b2c. The gate electrode 2b2a of the thin film transistor 2b2 can be electrically connected with the corresponding control line 2c1. The drain electrode 2b2b of the thin film transistor 2b2 can be electrically connected with the corresponding data line 2c2. The source electrode 2b2c of the thin film transistor 2b2 can be electrically connected to the corresponding photoelectric conversion element 2b1 and storage capacitor. Also, the storage capacitor and the anode side of the photoelectric conversion element 2b1 can be electrically connected to ground. The storage capacitor and the anode side of the photoelectric conversion element 2b1 also can be electrically connected to a not-illustrated bias line.

Multiple control lines 2c1 can be located parallel to each other with a prescribed spacing interposed. For example, the control line 2c1 can extend in a row direction.

One control line 2c1 can be electrically connected with one of the multiple interconnect pads 2d1 located at the peripheral edge vicinity of the substrate 2a. One of multiple interconnects provided in a flexible printed circuit board 2e1 can be electrically connected to one interconnect pad 2d1. The other ends of the multiple interconnects provided in the flexible printed circuit board 2e1 can be electrically connected respectively to read circuits 11a provided in the circuit board 11.

Multiple data lines 2c2 can be provided to be parallel to each other with a prescribed spacing interposed. For example, the data line 2c2 can extend in a column direction orthogonal to the row direction. One data line 2c2 can be electrically connected with one of the multiple interconnect pads 2d2 located at the peripheral edge vicinity of the substrate 2a. One of multiple interconnects provided in a flexible printed circuit board 2e2 can be electrically connected to one interconnect pad 2d2. The other ends of the multiple interconnects provided in the flexible printed circuit board 2e2 can be electrically connected respectively to signal detection circuits 11b provided in the circuit board 11.

For example, the control line 2c1 and the data line 2c2 can be formed using a low-resistance metal such as aluminum, chrome, etc.

The protective layer 2f can include a first layer 2f1 and a second layer 2f2. The first layer 2f1 can cover the photoelectric converter 2b, the control line 2c1, and the data line 2c2. The second layer 2f2 can be located on the first layer 2f1.

The first layer 2f1 and the second layer 2f2 can be formed from an insulating material. The insulating material can be, for example, an oxide insulating material, a nitride insulating material, an oxynitride insulating material, a resin, etc.

The scintillator 3 is located on the multiple photoelectric converters 2b and can convert the incident X-rays into fluorescence, i.e., visible light. The scintillator 3 can be provided to cover a region (an effective pixel region A) on the substrate 2a in which the multiple photoelectric converters 2b are located.

For example, the scintillator 3 can be formed using cesium iodide (CsI):thallium (TI), sodium iodide (NaI):thallium (TI), cesium bromide (CsBr):europium (Eu), etc. The scintillator 3 can be formed using vacuum vapor deposition. If the scintillator 3 is formed using vacuum vapor deposition, a scintillator 3 that is made of an aggregate of multiple columnar crystals is formed.

A mask that has an opening can be used when forming the scintillator 3 by using vacuum vapor deposition. In such a case, the scintillator 3 can be formed in a position facing the opening on the array substrate 2 (on the effective pixel region A). Also, a film that is formed by vapor deposition is formed on the surface of the mask. Then, at the vicinity of the opening of the mask, the film grows to gradually jut into the opening. When the film juts into the opening, the vapor deposition of the array substrate 2 is suppressed at the vicinity of the opening. Therefore, as shown in FIGS. 1 and 2, the thickness of the peripheral edge vicinity of the scintillator 3 gradually decreases outward.

Also, for example, the scintillator 3 can be formed using terbium-activated sulfated gadolinium ($Gd_2O_2S/Tb$ or GOS), etc. In such a case, a trench portion that has a matrix configuration can be provided so that a quadrilateral prism-shaped scintillator 3 is provided for each of the multiple photoelectric converters 2b.

The reflecting part 4 can be provided to increase the utilization efficiency of the fluorescence and improve the sensitivity characteristics. In other words, the reflecting part 4 can reflect the light of the fluorescence generated by the scintillator 3 and oriented toward the side opposite to the side at which the photoelectric converter 2b is located, and can cause the light to be oriented toward the photoelectric converter 2b. However, the reflecting part 4 is not always necessary; it is sufficient to provide the reflecting part 4 according to the necessary sensitivity characteristics of the X-ray detection module 10, etc.

A case where the reflecting part 4 is provided will now be described as an example.

The reflecting part 4 can be located on the scintillator 3. The reflecting part 4 can be located at the incident side of the X-rays of the scintillator 3. For example, the reflecting part 4 can be located to cover the region of an upper surface 3a of the scintillator 3 facing the effective pixel region A. For example, the reflecting part 4 can be formed by coating, onto the scintillator 3, a material in which a solvent, a resin, and light-scattering particles made of titanium oxide ($TiO_2$), etc., are mixed, and by drying the coating.

Also, for example, the reflecting part 4 can be formed by forming, on the scintillator 3, a layer made of a metal having high light reflectance such as a silver alloy, aluminum, etc. Also, for example, the reflecting part 4 can be made by bonding, onto the scintillator 3, a sheet having a surface made of a metal having high light reflectance such as a silver alloy, aluminum, or the like, a resin sheet including light-scattering particles, etc. In such a case, for example, the sheet and the scintillator 3 can be bonded using double-sided tape, etc.

The moisture-resistant part 5 can be provided to suppress degradation of the characteristics of the reflecting part 4 and the characteristics of the scintillator 3 due to moisture included in the air. The moisture-resistant part 5 can cover the scintillator 3 and the light-absorbing part 7. When the reflecting part 4 is provided, the moisture-resistant part 5 can cover the scintillator 3, the reflecting part 4, and the light-absorbing part 7. A gap may be between the moisture-resistant part 5, the reflecting part 4, etc.; or the moisture-resistant part 5, the reflecting part 4, etc., may be in contact. For example, if the array substrate 2 and the peripheral edge vicinity of the moisture-resistant part 5 are bonded in an environment depressurized from atmospheric pressure, the moisture-resistant part 5, the reflecting part 4, etc., can be in contact.

The moisture-resistant part 5 can be formed from a material that has a small moisture permeance. The moisture-resistant part 5 can include, for example, a metal. For example, the moisture-resistant part 5 can be formed from a metal that includes copper, a metal that includes aluminum, a metal such as stainless steel, a Kovar material, etc. For example, the moisture-resistant part 5 also can be formed from a stacked film in which a resin film and a metal film are stacked. In such a case, for example, the resin film can be formed from a polyimide resin, an epoxy resin, a polyethylene terephthalate resin, Teflon (registered trademark), low density polyethylene, high density polyethylene, elastic rubber, etc. For example, the metal film can be formed from a metal that includes copper, a metal that includes aluminum, a metal such as stainless steel, a Kovar material, etc. In such a case, if the moisture-resistant part 5 includes a metal, the moisture that permeates the moisture-resistant part 5 can be substantially completely eliminated.

Also, the thickness of the moisture-resistant part 5 can be determined by considering the absorption of the X-rays, the rigidity, etc. In such a case, the absorption of the X-rays becomes too large if the thickness of the moisture-resistant part 5 is too thick. The rigidity decreases and damage occurs more easily if the thickness of the moisture-resistant part 5 is too thin. For example, the moisture-resistant part 5 can be formed using an aluminum foil having a thickness of 0.1 mm.

As shown in FIG. 2, the bonding part 6 can be located between the array substrate 2 and the peripheral edge vicinity of the moisture-resistant part 5. The bonding part 6 bonds the array substrate 2 and the peripheral edge vicinity of the moisture-resistant part 5. For example, the bonding part 6 can be formed by curing an ultraviolet-curing adhesive, a two-component mixed adhesive, etc.

As shown in FIG. 1, the circuit board 11 can be located at the side opposite to the side at which the scintillator 3 of the array substrate 2 is located. The circuit board 11 can be electrically connected with the X-ray detection module 10 (the array substrate 2).

As shown in FIG. 3, the read circuit 11a and the signal detection circuit 11b can be located in the circuit board 11. These circuits can be provided in one substrate; or these circuits can be separated and provided in multiple substrates.

The read circuit 11a can switch between the on-state and the off-state of the thin film transistor 2b2. The read circuit 11a can include multiple gate drivers 11aa and a row selection circuit 11ab.

A control signal S1 can be input to the row selection circuit 11ab from a not-illustrated image processor, etc., located outside the X-ray detector 1. The row selection circuit 11ab can input the control signal S1 to the corresponding gate driver 11aa according to the scanning direction of the X-ray image.

The gate driver 11aa can input the control signal S1 to the corresponding control line 2c1. For example, the read circuit 11a can sequentially input the control signal S1 via the flexible printed circuit board 2e1 to each control line 2c1. The thin film transistor 2b2 is set to the on-state by the control signal S1 input to the control line 2c1; and a charge (an image data signal S2) from a storage capacitor can be read.

The signal detection circuit 11b can include multiple integrating amplifiers 11ba, multiple selection circuits 11bb, and multiple AD converters 11bc.

One integrating amplifier 11ba can be electrically connected with one data line 2c2. The integrating amplifier 11ba can sequentially receive the image data signals S2 from the photoelectric converters 2b. Then, the integrating amplifier 11ba can integrate the current flowing within a constant amount of time and can output a voltage corresponding to the integral to the selection circuit 11bb. Thus, the value (the charge amount) of the current flowing through the data line 2c2 can be converted into a voltage value within a prescribed period of time. In other words, the integrating amplifier 11ba can convert, into potential information, image data information that corresponds to the intensity distribution of the fluorescence generated by the scintillator 3.

The selection circuit 11bb can select the integrating amplifier 11ba that performs the reading, and can sequentially read the image data signals S2 converted into the potential information.

The AD converter 11bc can sequentially convert the image data signal S2 that is read into a digital signal. The image data signal S2 that is converted into the digital signal can be input to an image processor via an interconnect. The image data signal S2 that is converted into the digital signal may be transmitted to the image processor by a wireless technique.

The image processor can form an X-ray image based on the image data signal S2 converted into the digital signal. Also, the image processor can be integrated with the circuit board 11.

Here, as described above, the scintillator 3 is formed on the effective pixel region A by using vacuum vapor deposition and is formed by coating a material onto the effective pixel region A. Therefore, it is difficult to form the scintillator 3 only on the effective pixel region A. In other words, misalignment occurs due to the alignment precision between the effective pixel region A and the scintillator 3. In such a case, to prevent the peripheral edge vicinity of the effective pixel region A from being located outward of the scintillator 3, it is sufficient for the scintillator 3 to have larger dimensions than the effective pixel region A when viewed in plan. Therefore, generally, as shown in FIG. 2, the scintillator 3 is located also at the vicinity outside the effective pixel region A.

Also, the irradiation region of the X-rays incident on the X-ray detector 1 is set according to the size of the subject on which the X-rays are irradiated. Therefore, there are cases where X-rays also are irradiated outside the effective pixel region A.

The X-rays that are incident on the scintillator 3 are converted into fluorescence by the scintillator 3.

Figure 4:
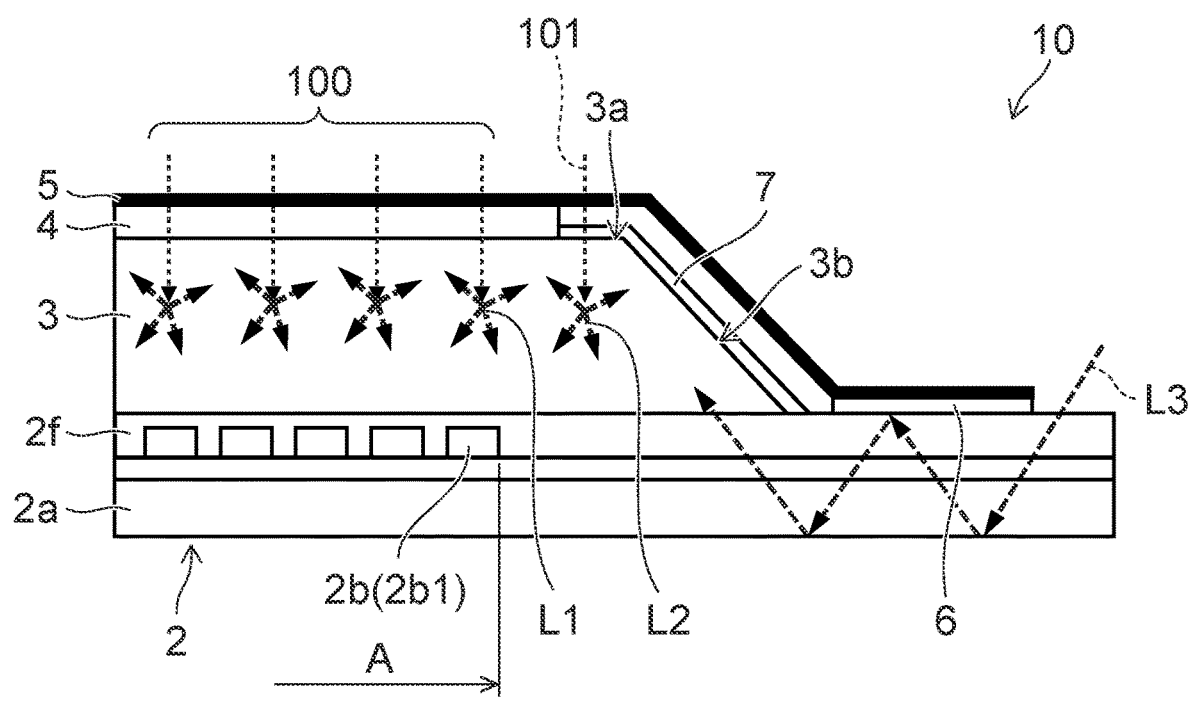
FIG. 4 is a schematic cross-sectional view for illustrating a state of the generation of fluorescence.

FIG. 4 is a schematic cross-sectional view for illustrating a state of the generation of fluorescence.

As shown in FIG. 4, fluorescence L1 that is generated by X-rays 100 incident on the effective pixel region A from above is incident on the photoelectric converters 2b (the photoelectric conversion elements 2b1) positioned below the fluorescence L1 and converted into a charge. On the other hand, for fluorescence L2 that is generated by X-rays 101 incident outside the effective pixel region A from above, the photoelectric converters 2b (the photoelectric conversion elements 2b1) are not below the fluorescence L2. Therefore, the fluorescence L2 is scattered without being converted into charge. There are cases where a portion of the scattered fluorescence L2 is reflected by the side surface 3b and/or the upper surface 3a of the scintillator 3 and is irradiated on the effective pixel region A.

Also, light-emitting diodes for checking the operation, etc., are provided inside the housing in which the X-ray detector 1 is located. Also, there are also cases where external light enters the interior of the housing through fine gaps in the housing. As described above, the substrate 2a is formed from glass. Therefore, as shown in FIG. 4, there are cases where light L3 such as the light emitted from the light-emitting diodes, external light, etc., enters the interior of the scintillator 3 via the substrate 2a. There are cases where the light L3 that enters the interior of the scintillator 3 is reflected by the side surface 3b and/or the upper surface 3a of the scintillator 3 and is irradiated on the effective pixel region A.

Therefore, when the fluorescence L2 and/or the light L3 occurs, there is a risk that the fluorescence L1 generated above the photoelectric conversion elements 2b1 and the fluorescence L2 and/or the light L3 may mix and be incident on the photoelectric conversion elements 2b1.

Also, when a large amount of X-ray irradiation on the human body is performed, the X-ray irradiation amount on the human body is suppressed as much as possible due to the unfavorable effects on health. Therefore, the intensity of the X-rays incident on the X-ray detector 1 is extremely low, and the intensity of the fluorescence generated by the scintillator 3 is extremely low. Therefore, the photoelectric conversion elements 2b1 that are located in the X-ray detector 1 are extremely highly-sensitive. As a result, the fluorescence L2 and/or the light L3 is more easily converted into charge by the photoelectric conversion elements 2b1.

Compared to an X-ray image formed from the image data signal S2 into which the components due to the fluorescence L2 and/or the light L3 are not mixed, there is a risk that an X-ray image that is formed from the image data signal S2 into which the components due to the fluorescence L2 and/or the light L3 are mixed may have low image contrast, increased image noise, and poor image quality.

Therefore, the light-absorbing part 7 is provided in the X-ray detector 1 according to the embodiment.

As shown in FIG. 1, FIG. 2, and FIG. 4, the light-absorbing part 7 can be located on the scintillator 3. The light-absorbing part 7 can be located outward of the effective pixel region A when viewed in plan. For example, the light-absorbing part 7 can be located at the side surface 3b of the scintillator 3. Also, when the reflecting part 4 is provided, the light-absorbing part 7 can be located outward of the reflecting part 4 when viewed in plan. For example, the light-absorbing part 7 can be located outside the reflecting part 4 at the upper surface 3a of the scintillator 3 and at the side surface 3b of the scintillator 3.

The light-absorbing part 7 can be capable of absorbing visible light. The light-absorbing part 7 can include a color that is capable of absorbing visible light. In such a case, it is favorable for the color of the light-absorbing part 7 to be, for example, black or a color approximating black. If the color of the light-absorbing part 7 is black or a color approximating black, the fluorescence L2 and/or the light L3 described above is easily absorbed. The color approximating black can be, for example, a mixed color of black and blue (e.g., dark blue), a mixed color of black and red (e.g., brown), etc.

When the color of the light-absorbing part 7 is black, the light-absorbing part 7 can include, for example, a carbon-based black pigment, an oxide-based black pigment, etc. The carbon-based black pigment can be, for example, carbon black, graphite, etc. The oxide-based black pigment can be, for example, an oxide of iron, a hybrid oxide of copper and chrome, a hybrid oxide of copper, chrome, and zinc, etc.

The thickness of the light-absorbing part 7 is not particularly limited. The thickness of the light-absorbing part 7 can be, for example, about 1 μm.

For example, the light-absorbing part 7 can be formed by coating a material in which a solvent, a resin, and a pigment of black or a color approximating black is mixed onto the surface of the scintillator 3 and by drying the coating.

Also, the light-absorbing part 7 can be formed by, for example, discoloring the surface of the scintillator 3 to be brown or the like by irradiating ultraviolet light, etc., on the surface of the scintillator 3.

When the aforementioned fluorescence L2 and/or the light L3 is incident on the light-absorbing part 7, a portion of the fluorescence L2 and/or the light L3 is absorbed by the light-absorbing part 7. Therefore, even when the fluorescence L2 and/or the light L3 occurs, the amount of the fluorescence L2 and/or the light L3 incident on the photoelectric conversion element 2b1 can be reduced. As a result, the low image contrast and the increased image noise can be suppressed; therefore, an improvement of the image quality can be realized.

(Method for Manufacturing X-Ray Detection Module 10 and Method for Manufacturing X-Ray Detector 1)

First, the array substrate 2 is manufactured by sequentially forming the control line 2c1, the data line 2c2, the interconnect pad 2d1, the interconnect pad 2d2, the photoelectric converter 2b, the protective layer 2f, etc., on the substrate 2a. For example, the array substrate 2 can be manufactured using a semiconductor manufacturing process. Known technology is applicable to the manufacturing of the array substrate 2, and a detailed description is therefore omitted.

Then, the scintillator 3 is formed to cover the effective pixel region A of the substrate 2a.

For example, the scintillator 3 can be formed using vacuum vapor deposition. If the scintillator 3 is formed using vacuum vapor deposition, the scintillator 3 that is made of an aggregate of multiple columnar crystals is formed. The thickness of the scintillator 3 can be modified as appropriate according to the DQE characteristics, the sensitivity characteristics, the resolution characteristics, etc., that are necessary for the X-ray detector 1. The thickness of the scintillator 3 can be, for example, about 600 μm.

Also, a quadrilateral prism-shaped scintillator 3 may be provided for each of the multiple photoelectric converters 2b by mixing a light-emitting substance and a binder material, coating the mixed material to cover the effective pixel region A, firing the coating, and forming a trench portion having a matrix configuration in the fired material.

Then, the reflecting part 4 is formed on the scintillator 3 as necessary.

For example, the reflecting part 4 can be formed by coating, onto the scintillator 3, a material in which a solvent, a resin, and multiple light-scattering particles are mixed and by drying the coating. Also, for example, the reflecting part 4 also can be formed by forming a layer made of a metal having high light reflectance on the scintillator 3, or by bonding a resin sheet including light-scattering particles, etc., on the scintillator 3.

Then, the light-absorbing part 7 is formed on the scintillator 3.

For example, the light-absorbing part 7 can be formed in a region of the surface of the scintillator 3 positioned outward of the effective pixel region A when viewed in plan by coating a material in which a solvent, a resin, and a pigment are mixed and by drying the coating.

Also, the light-absorbing part 7 can be formed by, for example, discoloring the surface of the scintillator 3 brown, etc., by irradiating ultraviolet light, etc., on the surface of the scintillator 3.

Then, the moisture-resistant part 5 is provided to cover the scintillator 3 and the light-absorbing part 7. When the reflecting part 4 is provided, the moisture-resistant part 5 is provided to cover the scintillator 3, the reflecting part 4, and the light-absorbing part 7. For example, the peripheral edge vicinity of the sheet-like or hat-shaped moisture-resistant part 5 can be bonded to the array substrate 2. In such a case, the bonding part 6 is formed by curing an adhesive.

If the moisture-resistant part 5 is bonded to the array substrate 2 in an environment depressurized from atmospheric pressure, the storage of air including water vapor inside the moisture-resistant part 5 can be suppressed. Also, even when the X-ray detector 1 is located in an environment depressurized from atmospheric pressure such as when the X-ray detector 1 is transported by an aircraft, etc., the expansion and the deformation of the moisture-resistant part 5 due to the air inside the moisture-resistant part 5 can be suppressed. Also, the moisture-resistant part 5 is closely adhered to the scintillator 3, etc., because the moisture-resistant part 5 is pressed by atmospheric pressure.

Thus, the X-ray detection module 10 can be manufactured.

Then, the array substrate 2 and the circuit board 11 are electrically connected via the flexible printed circuit boards 2e1 and 2e2.

Other circuit components, etc., are mounted as appropriate.

Then, the array substrate 2, the circuit board 11, etc., are housed inside a not-illustrated housing.

Also, an X-ray image test, an electrical test that checks the existence or absence of an abnormality of the photoelectric conversion element 2b1 and/or the existence or absence of an abnormality of the electrical connection, etc., are performed as necessary.

Thus, the X-ray detector 1 can be manufactured.

A high-temperature high-humidity test, a temperature cycle test, etc., also can be performed to check the moisture resistance reliability of the product and/or the reliability with respect to the change of the thermal environment.

As described above, the method for manufacturing the X-ray detection module 10 according to the embodiment can include the following processes.

A process of forming the scintillator 3 that covers the region (the effective pixel region A) in which the multiple photoelectric converters 2b are located, and that has larger dimensions than the region in which the multiple photoelectric converters 2b are located when viewed in plan.

A process of forming, on the scintillator 3, the light-absorbing part 7 that is capable of absorbing visible light.

In such a case, the light-absorbing part 7 is formed outward of the region in which the multiple photoelectric converters 2b are located when viewed in plan.

When forming the light-absorbing part 7, the surface of the scintillator 3 can be discolored by irradiating ultraviolet light on the surface of the scintillator 3.

When forming the light-absorbing part 7, a material that includes a pigment can be coated onto the surface of the scintillator 3.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions. Moreover, above-mentioned embodiments can be combined mutually and can be carried out.

What is claimed is:

1. A radiation detection module, comprising:
    an array substrate including a plurality of photoelectric converters;
    a scintillator covering a region in which the plurality of photoelectric converters is located, the scintillator having larger dimensions than the region in which the plurality of photoelectric converters is located when viewed in plan; and
    a light-absorbing part located at a side surface and an upper surface of the scintillator, the light-absorbing part being configured to absorb visible light, the light-absorbing part including a material of a surface part of the scintillator that has been discolored by ultraviolet light,
    the light-absorbing part being located outward of the region in which the plurality of photoelectric converters is located when viewed in plan.

2. The radiation detection module according to claim 1, wherein a color of the light-absorbing part is black or a color approximating black.

3. The radiation detection module according to claim 2, wherein the color approximating black is dark blue or brown.

4. The radiation detection module according to claim 1, wherein a material of the scintillator is one of cesium iodide (CsI):thallium (Tl), sodium iodide (NaI):thallium (Tl), and cesium bromide (CsBr):europium (Eu).

5. The radiation detection module according to claim 1, wherein a material of the scintillator is terbium-activated sulfated gadolinium ($Gd_2O_2S$/Tb).

6. The radiation detection module according to claim 1, wherein
    the scintillator converts the radiation that is incident on the scintillator into fluorescence, and
    a portion of the fluorescence generated by the radiation incident on the scintillator is absorbed by the light-absorbing part outward of the region in which the plurality of photoelectric converters is located.

7. The radiation detection module according to claim 1, wherein a portion of external light penetrating the scintillator via the array substrate is absorbed by the light-absorbing part.

8. The radiation detection module according to claim 1, wherein the reflecting part includes a light-scattering particle and a resin.

9. The radiation detection module according to claim 1, wherein the reflecting part includes a metal.

10. A radiation detector, comprising:
    the radiation detection module according to claim 1; and
    a circuit board electrically connected with the radiation detection module.

11. A method for manufacturing a radiation detection module, the method comprising:
    forming a scintillator, the scintillator covering a region in which a plurality of photoelectric converters is located, the scintillator having larger dimensions than the region in which the plurality of photoelectric converters is located when viewed in plan; and forming a light-absorbing part at a side surface and an upper surface of the scintillator, the light-absorbing part being configured to absorb visible light, the forming of the light-absorbing part including discoloring the side surface and the upper surface of the scintillator by irradiating ultraviolet light on the surface of the scintillator, the light-absorbing part being formed outward of the region in which the plurality of photoelectric converters is located when viewed in plan.

* * * * *